(12) United States Patent
Azuma et al.

(10) Patent No.: US 11,491,095 B2
(45) Date of Patent: Nov. 8, 2022

(54) OILY MAKEUP COSMETIC

(71) Applicant: KOSE CORPORATION, Tokyo (JP)

(72) Inventors: Ryuta Azuma, Tokyo (JP); Ryo Kakimoto, Tokyo (JP); Takayuki Kimura, Tokyo (JP)

(73) Assignee: KOSE CORPORATION, Tokyo (JP)

( * ) Notice: Subject to any disclaimer, the term of this patent is extended or adjusted under 35 U.S.C. 154(b) by 150 days.

(21) Appl. No.: 16/349,568

(22) PCT Filed: Nov. 14, 2017

(86) PCT No.: PCT/JP2017/040851
§ 371 (c)(1),
(2) Date: May 13, 2019

(87) PCT Pub. No.: WO2018/088565
PCT Pub. Date: May 17, 2018

(65) Prior Publication Data
US 2020/0179256 A1   Jun. 11, 2020

(30) Foreign Application Priority Data

Nov. 14, 2016  (JP) ............................. JP2016/221285
Nov. 14, 2016  (JP) ............................. JP2016-221286

(51) Int. Cl.
*A61Q 1/06*  (2006.01)
*A61K 8/49*  (2006.01)
*A61K 8/41*  (2006.01)
*A61K 8/92*  (2006.01)

(52) U.S. Cl.
CPC ............ *A61K 8/4966* (2013.01); *A61K 8/418* (2013.01); *A61K 8/92* (2013.01); *A61Q 1/06* (2013.01)

(58) Field of Classification Search
None
See application file for complete search history.

(56) References Cited

U.S. PATENT DOCUMENTS

| | | | | |
|---|---|---|---|---|
| 2014/0030202 A1* | 1/2014 | Simonnet | ............... | A61Q 19/00 424/63 |
| 2014/0356403 A1 | 12/2014 | Zhu et al. | ..................... | 424/401 |
| 2016/0143837 A1 | 5/2016 | Liu | | |
| 2017/0319454 A1 | 11/2017 | Oohashi et al. | | |

FOREIGN PATENT DOCUMENTS

| | | | |
|---|---|---|---|
| EP | 3 449 898 A1 | 3/2019 | |
| JP | 08-157323 A | 6/1996 | |
| JP | 2004-175773 A | 6/2004 | |
| JP | 2014-24766 A | 2/2014 | |
| JP | 2016-132650 A | 7/2016 | |
| JP | 2016124863 A | * 7/2016 | |
| JP | 2016-185921 A | 10/2016 | |
| JP | 3 248 589 A1 | 11/2017 | |
| JP | 2017-197492 A | 11/2017 | |
| WO | WO 2017/188360 A1 | 11/2017 | |

OTHER PUBLICATIONS

Japanese Office Action dated Oct. 15, 2019, issued to Japanese Application No. 2018-550302.
Third Party Observation dated Aug. 23, 2018, issued to International Application No. PCT/JP2017/040851.
Extended European Search Report dated May 14, 2020, issued to European Application No. 17870108.2.
Database GNPD [Online], MINTEL; Apr. 6, 2015; "Your Lip Only Gloss", XP55691459, retrieved from www.gnpd.com; Database accession No. 3215725.
Database GNPD [Online], MINTEL;Nov. 1, 2012; "Magic Color Gloss", XP55691461, retrieved from www.gnpd.com: Database accession No. 1710203.
Database GNPD [Online], MINTEL; Jul. 5, 2016; "Lip Color Stain", XP055692246, retrieved from www.gnpd.com; Database accession No. 4298045.
Japanese Office Action dated Jun. 2, 2020, issued to Japanese Application No. 2018-550302.
Chinese Office Action dated Oct. 29, 2021, issued to corresponding Chinese Application No. 201780069982.1.
Taiwanese Office Action dated Aug. 4, 2021, issued to corresponding Taiwanese Patent No. 106139337.
Korean Office Action dated Apr. 11, 2022, issued to Korean Application No. 10-2019-7013587.
European Office Action dated Feb. 10, 2022, issued to European Application No. 17 870 108.2-1112.
Chinese Office Action dated Apr. 19, 2022, issued to the corresponding Chinese Application No. 201780069982.1.

* cited by examiner

*Primary Examiner* — Jyothsna A Venkat
(74) *Attorney, Agent, or Firm* — Stein IP, LLC (57) ABSTRACT

The present invention is intended to provide an oily makeup cosmetic that is colorless in appearance but develops a color on application onto body surface, such as skin and lips. The present invention provides a colorless oily makeup cosmetic comprising (a) one or two dyes selected from Red No. 218 and Red No. 223, and (b) an oil agent, and a mixture of the component (a) and the component (b) at a mass ratio (a):(b) of 0.1:100 has a difference of 0.2 or less between the maximum absorbance and the minimum absorbance in a wavelength region of 500 to 600 nm. The oily makeup cosmetic may develop a color due to the component (a) on application onto body surface, such as skin and lips.

4 Claims, 1 Drawing Sheet

OILY MAKEUP COSMETIC

CROSS-REFERENCE TO RELATED APPLICATIONS

This application is a national stage of International Application No. PCT/JP2017/040851, filed Nov. 14, 2017, which claims the benefit of priority to Japanese Application No. 2016-221285, filed Nov. 14, 2016, and Japanese Application No. 2016-221286, filed Nov. 14, 2016, in the Japanese Patent Office, the disclosures of which are incorporated herein by reference.

TECHNICAL FIELD

The present invention relates to an oily makeup cosmetic that is colorless in appearance but develops a color on application onto body surface, such as skin and lips.

BACKGROUND ART

Oily makeup cosmetics are makeup cosmetics containing an oil phase as a continuous phase. The oily makeup cosmetics have excellent long-lasting makeup properties and thus are often used as makeup cosmetics including lipsticks, lip glosses, cheek rouges, and eye shadows. To allow a makeup cosmetic to develop a bright red color, a dye such as Red No. 218 and Red No. 223 has been widely used. For example, Patent Document 1 discloses a solid cosmetic comprising an oil agent, a dextrin fatty acid ester, dipropylene glycol, and a dye. Dyes are known to be easily discolored depending on environmental factors such as water content, light, and temperature, and techniques for allowing a cosmetic to stably contain a dye have been studied. For example, Patent Document 2 discloses a composition in which a dye is dispersed or dissolved in an aqueous solution of a polyoxyethylene addition nonionic surfactant, in the presence of a water-soluble antioxidant. Patent Document 3 discloses a makeup cosmetic comprising a particular oil-soluble dye, particles of a particular material, and oil.

CITATION LIST

Patent Document

Patent Document 1: JP-A No. 2004-175773
Patent Document 2: JP-A No. 2014-24766
Patent Document 3: JP-A No. 2016-138095

SUMMARY OF THE INVENTION

Technical Problem

Due to recent diversifications in preference, there is a demand for a cosmetic differing between color in appearance and color after application onto body surface, such as skin and lips. In particular, there has been a strong demand for makeup cosmetics, such as lipsticks, lip glosses, cheek rouges, and eye shadows, differing between color in appearance and color after application on a body surface.

However, the cosmetic according to Patent Document 1 has the same color in appearance as that after application, and is difficult to achieve the quality requirements in the recent market. The cosmetic according to Patent Document 1 is also inferior in light stability and high-temperature stability.

The composition according to Patent Document 2 comprises, as essential components, a water-soluble antioxidant and a polyoxyethylene addition nonionic surfactant, and thus does not achieve satisfactory long-lasting makeup properties. It may also be difficult to make the composition according to Patent Document 2 an oily makeup cosmetic.

The cosmetic according to Patent Document 3 also already develops a color due to the dye before application onto skin or lips.

Therefore, the present invention is intended to provide an oily makeup cosmetic that is colorless in appearance but develops a color on application onto body surface, such as skin and lips.

Solution to Problem

As a result of intensive studies, the inventors of the present invention have found that by combination of a specific dye exhibiting red and a specific oil agent, an oily makeup cosmetic that is colorless in appearance but develops a color on application onto body surface, such as skin and lips, may be provided, and have completed the present invention. The inventors of the present invention have also found that when further adding a specific component, the oily makeup cosmetic obtains higher high-temperature stability and/or higher light stability.

The present invention provides a colorless oily makeup cosmetic comprising (a) one or two dyes selected from Red No. 218 and Red No. 223, and (b) an oil agent, and a mixture of the component (a) and the component (b) at a mass ratio (a):(b) of 0.1:100 has a difference of 0.2 or less between a maximum absorbance and a minimum absorbance in a wavelength region of 500 to 600 nm.

According to an aspect of the present invention, the component (b) may be one or two or more oil agents selected from triethylhexanoin, tritridecyl trimellitate, dialkyl carbonate (C14, C15), polyglyceryl-10 decaethylhexanoate, diisostearyl malate, mineral oil, hydrogenated polyisobutene, methylphenylpolysiloxane, dimethylpolysiloxane, and polyglyceryl-2 triisostearate having emery type isostearic acid groups.

According to an aspect of the present invention, the oily makeup cosmetic may develop a color on application onto skin and/or a lip.

According to an aspect of the present invention, the oily makeup cosmetic may further comprise (c) one or two or more polymers selected from a carboxyvinyl polymer and an alkyl-modified carboxyvinyl polymer.

According to an aspect of the present invention, a content mass ratio of the component (a) to the component (c), (a)/(c), may be 0.1 to 2.0.

According to an aspect of the present invention, the oily makeup cosmetic may further comprise (d) an oily gelling agent.

According to an aspect of the present invention, the oily makeup cosmetic may be liquid at 25° C.

According to an aspect of the present invention, the oily makeup cosmetic may have a dynamic viscosity of 10,000 to 20,000 cs at 25° C.

According to an aspect of the present invention, a content rate of the component (b) may be 65 to 99.9% by mass relative to a mass of the cosmetic.

According to an aspect of the present invention, a content rate of the component (a) may be 0.01 to 1.0% by mass relative to the mass of the cosmetic.

According to an aspect of the present invention, a content rate of the component (c) may be 0.01 to 1.0% by mass relative to the mass of the cosmetic.

Advantageous Effects of Invention

The oily makeup cosmetic of the present invention is colorless in appearance but develops a color on application onto skin, lips, or another body surface.

DESCRIPTION OF EMBODIMENTS

The present invention will now be described in detail. In the present specification, "to" means a range including the numerical values before and after it.

Red No. 218 and Red No. 223 as a component (a) contained in a cosmetic of the present invention are fluorene type oil-soluble dyes and may be classified into tar dyes. Red No. 218 and Red No. 223 develop a red color and thus are coloring agents widely used in makeup cosmetics including lipsticks. However, cosmetics containing such a dye may be faded by light. To address this problem, such a cosmetic is required not to be exposed to light by using a light-resistant container or the like. Examples of the commercial products include TPP Red No. 218 and TPP Red No. 223 (manufactured by Kishi Kasei Co., Ltd.).

The generic name of Red No. 218 is tetrachlorotetrabromofluorescein. The CAS register number of Red No. 218 is 13473-26-2, the CI number is 45410:1, the CI name is Solvent RED 48, and the FDA name is D&C Red No. 27. The chemical name of Red No. 218 is 2',4',5',7'-tetrabromo-4,5,6,7-tetrachloro-3',6'-dihydroxyspiro[isobenzofuran-1(3H),9'-[9H]xanthen]-3-one, and has the following chemical structure.

[Chemical Formula 1]

$C_{2n}H_4Br_4Cl_4O_5$:785.67

The generic name of Red No. 223 is tetrabromofluorescein. The CAS register number of Red No. 223 is 15086-94-9, the CI number is 45380:2, the CI name is Solvent RED 43, and the FDA name is D&C Red No. 21. The chemical name of Red No. 223 is 2',4',5',7'-tetrabromo-3',6'-dihydroxyspiro[isobenzofuran-1(3H),9'-[9H]xanthen]-3-one, and has the following chemical structure.

[Chemical Formula 2]

$C_{2n}H_3Br_4O_6$:647.89

In the cosmetic of the present invention, the content rate of the component (a) is preferably 0.01 to 1.0% by mass (in the present specification, "%" means "% by mass" unless otherwise specified), more preferably 0.02 to 0.1%, and even more preferably 0.03 to 0.1% relative to the total mass of the cosmetic of the present invention. When the content rate of the component (a) is within the range, the cosmetic of the present invention may have more excellent dyeing performance and more excellent transparency.

The component (b) contained in the cosmetic of the present invention is such an oil agent that a mixture of the component (a) and the component (b) at a mass ratio (a):(b) of 0.1:100 has a difference of 0.2 or less between the maximum absorbance and the minimum absorbance in a wavelength region of 500 to 600 nm. The component (b) may be an oil agent commonly used in cosmetics. Examples of the form of the oil agent as the component (b) include, but are not limited to, a solid form, a semi-solid form, and a liquid form. The oil agent as the component (b) may be preferably liquid at 25° C. because advantageous effects of the present invention are markedly exerted.

The absorbances may be determined by measuring absorbances from 500 to 600 nm using a transparent polystyrene cell having an optical path length of 1 cm in an environment at 25° C. The absorbances may be determined with a commercially available absorbance measuring apparatus, and may be measured with an absorptiometer UV-2500PC manufactured by Shimadzu Corporation.

Examples of the component (b) used in the present invention include, but are not limited to,
ester oils such as triethylhexanoin, tritridecyl trimellitate, dialkyl carbonate (C14, C15), polyglyceryl-10 decaethylhexanoate, diisostearyl malate, and polyglyceryl-2 triisostearate having emery type isostearic acid groups;
hydrocarbon oils such as mineral oil and hydrogenated polyisobutene; and
silicone oils such as methylphenylpolysiloxane and dimethylpolysiloxane.

As the component (b), one or two or more of these compounds may be used.

Preferably, from the viewpoint of achieving more excellent light stability, the following compounds are more preferably used as the component (b):
of the ester oils, specifically, triethylhexanoin, tritridecyl trimellitate, dialkyl carbonate (C14, C15), polyglyceryl-10 decaethylhexanoate, or diisostearyl malate;

of the hydrocarbon oil, specifically, mineral oil or a hydrogenated polyisobutene having a dynamic viscosity of 10,000 cs or less at 40° C. or having an average molecular weight of 1,000 or less;

of the silicone oils, specifically, methylphenylpolysiloxane or a dimethylpolysiloxane having a dynamic viscosity of 10,000 cs or less at 25° C. or having an average molecular weight of 60,000 or less; or a combination of two or more of these compounds.

The emery type isostearic acid is a methyl-branched isostearic acid and may be obtained, for example, as a by-product in production of a dimer of oleic acid [for example, described in J. Amer. Oil Chem. Soc., 51, 522 (1974)]. Examples of the commercial product of the emery type isostearic acid include products that were commercially available from, for example, Emery Industries, Inc., USA. The starting material of the dimer acid as the starting material of the emery type isostearic acid may include not only oleic acid but also linoleic acid and linolenic acid, for example.

Generally, isostearic acid includes three isomers. The three types of isostearic acid are 2-heptylundecanoic acid, 2-isoheptylisoundecanoic acid, and an isostearic acid having an undetermined structure. The emery type isostearic acid is the isostearic acid having an undetermined structure, and is neither 2-heptylundecanoic acid nor 2-isoheptylisoundecanoic acid. The emery type isostearic acid is thought to have a methyl group as a side chain, but the position of the methyl group is undetermined. In particular, for the reason, the structure of the emery type isostearic acid is unknown.

Examples of the commercial product of the component (b) include Cosmol 43V (manufactured by Nisshin OilliO, polyglyceryl triisostearate having emery type isostearic acid groups), MYRITOL GTEH (manufactured by BASF, triethylhexanoin), DOCADIT TM-13N (manufactured by Nisshin OilliO, tritridecyl trimellitate), LIALCARB SR-1000/R (manufactured by Mitsui Fine Chemical Inc., dialkyl carbonate (C14, C15)), KEH-1010 (manufactured by Sakamoto Yakuhin kogyo Co., Ltd., polyglyceryl-10 decaethylhexanoate), Esterol DISM (manufactured by National Mimatsu Co., Ltd., diisostearyl malate), KLEAROL WHITE MINERAL OIL (manufactured by SONNEBORN, mineral oil), Purified Polybutene HV-100F (SB) (manufactured by Japan Natural Products, hydrogenated polyisobutene), Nisseki Polybutene HV-1900F (manufactured by JXTG Nippon Oil & Energy Corporation, hydrogenated polyisobutene), Silicone KF-56 (manufactured by Shin-Etsu Chemical Co., Ltd., methylphenylpolysiloxane), SH200C FLUID 6CS (manufactured by Dow Corning Toray Silicone Co., Ltd., dimethylpolysiloxane), and KF-96H-100,000CS (manufactured by Shin-Etsu Chemical Co., Ltd., dimethylpolysiloxane). As the component (b), one or two or more of them may be used.

In the cosmetic of the present invention, the content rate of the component (b) is preferably 65 to 99.9% by mass, more preferably 85 to 98.6% by mass, and even more preferably 92.7 to 98.6% by mass relative to the total mass of the cosmetic of the present invention. When the content rate of the component (b) is within the range, the component (a) may be more easily prevented from developing a color.

The cosmetic of the present invention may comprise an additional liquid component other than the component (b), but the content rate of the additional liquid component other than the component (b) contained in the cosmetic of the present invention is preferably 0.5% or less, more preferably 0.3% or less, and even more preferably 0.1% or less relative to the total mass of the cosmetic of the present invention. Accordingly, most of the liquid component in the cosmetic of the present invention is preferably the component (b). When the content rate of the additional liquid component other than the component (b) is within the range, the appearance of the cosmetic of the present invention may be more easily made colorless, and consequently, a cosmetic having excellent aesthetic quality may be obtained when packed in a transparent container.

In the present invention, the additional liquid component other than the component (b) is a component that is liquid in an environment at 25° C. The additional liquid component other than the component (b) may be a material commonly used in cosmetics. Examples of the additional liquid component other than the component (b) include polyhydric alcohols such as butylene glycol and dipropylene glycol, ester oils such as polyglyceryl-10 decastearate and polyglyceryl-2 triisostearate having aldol type isostearic acid groups, and polymers such as (vinylpyrrolidone/hexadecene) copolymers, and one or two or more of them may be used.

The aldol type isostearic acid is, for example, the isostearic acid compound represented by Chemical Formula (3). The aldol type isostearic acid corresponds to the above-described 2-isoheptylisoundecanoic acid. The isostearic acid represented by Chemical Formula (3) may be synthesized, for example, from an alpha-olefin having a side chain as a starting material by aldol condensation reaction but may be obtained by another synthetic method as long as the isostearic acid has the structure represented by Chemical Formula (3).

[Chemical Formula 3]

(3)

Examples of the commercial product of the additional liquid component other than the component (b) include NIKKOL DECAGLYN 10-ISV (manufactured by Nikko Chemicals Co., Ltd.), ANTARON V216 (manufactured by ISP Japan), and Cosmol 43N (manufactured by Nisshin OilliO), and one or two or more of them may be used.

According to a preferred embodiment of the present invention, the cosmetic of the present invention may comprise a carboxyvinyl polymer and/or an alkyl-modified carboxyvinyl polymer as a component (c).

The carboxyvinyl polymer may be, for example, a polymer mainly composed of acrylic acid and cross-linked with a small amount of allylsucrose. In the present invention, the component (c) is not limited to the above polymer and may be another carboxyvinyl polymer commonly used in cosmetics.

The alkyl-modified carboxyvinyl polymer may be an alkylated carboxyvinyl polymer, for example. As the alkyl-modified carboxyvinyl polymer, a compound commonly used in cosmetics may be used. In particular, the alkyl group of the alkylated polymer preferably has 10 to 30 carbon atoms. As the alkyl-modified carboxyvinyl polymer, an (acrylic acid/alkyl (C10-30) acrylate) copolymer is particularly preferred. Such a copolymer preferably has an average molecular weight of about 50,000 to 3,000,000 and more preferably 750,000 or more.

Examples of the commercial product of the carboxyvinyl polymer include Carbopol 940, Carbopol 941, and Carbopol 980 (manufactured by LUBRIZOL ADVANCED MATERIALS). Examples of the commercial product of the alkyl-modified carboxyvinyl polymer include PEMULEN TR-1, PEMULEN TR-2, Carbopol 1342, and Carbopol 1382 (manufactured by LUBRIZOL ADVANCED MATERIALS). As the component (c) used in the present invention, one or two or more of them may be used. Of them, an alkyl-modified carboxyvinyl polymer is more preferably used as the component (c) used in the present invention from the viewpoint of more excellent effect of suppressing discoloration of the component (a) at high temperature, for example.

The content rate of the component (c) used in the present invention is preferably 0.01 to 1.0%, more preferably 0.02 to 0.5%, and even more preferably 0.03 to 0.1% relative to the total mass of the cosmetic of the present invention. When the content rate of the component (c) is within the range, for example, the cosmetic of the present invention may have more excellent high-temperature stability and/or transparency.

In the present invention, the content mass ratio of the component (a) and the component (c), (a)/(c), is preferably 0.1 to 2.0 and more preferably 0.3 to 0.8. When the content mass ratio of the component (a) and the component (c) are within the range, the cosmetic of the present invention may have more excellent high-temperature stability and/or transparency.

According to a preferred embodiment of the present invention, the cosmetic of the present invention may further comprise a component (d), an oily gelling agent. As the oily gelling agent, a compound commonly used in cosmetics may be used. In other words, the present invention provides an oily makeup cosmetic comprising the components (a), (b), and (d). The present invention also provides an oily makeup cosmetic comprising the components (a), (b), (c), and (d).

Examples of the component (d) include dextrin octanoate, dextrin laurate, dextrin palmitate, dextrin myristate, dextrin stearate, dextrin behenate, dextrin coconut oil fatty acid, dextrin (palmitate/octanoate), sucrose fatty acid ester, starch fatty acid ester, 12-hydroxystearic acid, calcium stearate, silica, silica dimethyl silylate, polyethylene wax, (ethylene/propylene) copolymers, paraffin wax, montan wax, Fischer-Tropsch wax, ceresin wax, and ozokerite wax. The cosmetic of the present invention may comprise one or two or more of them as the component (d). Preferably, the component (d) may be, of the above compound group, one or two or more compounds selected from dextrin octanoate, dextrin laurate, dextrin palmitate, dextrin myristate, dextrin stearate, dextrin behenate, dextrin coconut oil fatty acid, dextrin (palmitate/octanoate), sucrose fatty acid ester, starch fatty acid ester, 12-hydroxystearic acid, calcium stearate, silica, and silica dimethyl silylate. When one or two or more compounds selected from these compounds are contained in the cosmetic of the present invention, a cosmetic having excellent transparency may be obtained, and consequently, the cosmetic packed in a transparent container has excellent aesthetic quality. The silica and silica dimethyl silylate are preferably fumy from the viewpoint of gelation ability, and the silica and silica dimethyl silylate may have an average primary particle size of, for example, 1 to 50 nm, specifically 3 to 40 nm, and more specifically 5 to 30 nm.

The content rate of the component (d) is preferably 0.1 to 10% and more preferably 1 to 7% relative to the total mass of the cosmetic of the present invention. When the content rate of the component (d) is within the range, the cosmetic of the present invention obtains viscosity, and consequently, the cosmetic of the present invention may have excellent feeling of use and long-lasting makeup properties.

The oily makeup cosmetic of the present invention preferably has a dynamic viscosity of 10,000 to 20,000 cs and specifically preferably 12,500 to 17,500 cs at 25° C. When the dynamic viscosity is within the numerical range, the component (a) may more rapidly develop a color on body surface, such as skin and lips. In the present invention, the dynamic viscosity is a value determined by the measurement method in accordance with ASTM D445 at 25° C.

According to another preferred embodiment of the present invention, the cosmetic of the present invention may further comprise, in addition to the components (a) and (b), a component (e), a hydrocarbon solid oil. In other words, the present invention also provides an oily makeup cosmetic comprising the components (a), (b), and (e). The present invention also provides an oily makeup cosmetic comprising the components (a), (b), (c), and (e). As the hydrocarbon solid oil, a compound commonly used in cosmetics may be used. When the component (e) is contained in the cosmetic of the present invention, the cosmetic may be colorless before application but may develop a color and be solid after application.

Examples of the component (e) include (ethylene/propylene) copolymers, paraffin wax, ceresin wax, microcrystalline wax, polyethylene wax, montan wax, and Fischer-Tropsch wax.

The content rate of the component (e) is preferably 1 to 15%, more preferably 2 to 13%, and even more preferably 3 to 10% relative to the total mass of the cosmetic of the present invention. When the content rate of the component (e) is within the range, the cosmetic of the present invention may be solid.

The oily makeup cosmetic of the present invention may appropriately comprise, in addition to the above components (a) to (e), components commonly used in cosmetics, such as a powder, a surfactant, a water-soluble polymer, a p-hydroxybenzoic acid derivative, an antiseptic agent, a solid ultraviolet absorber, a moisturizer, an antimicrobial agent, a flavoring agent, salts, an antioxidant, a pH adjuster, a chelating agent, an algefacient, an anti-inflammatory agent, a skin-beautifying component (a whitening agent, a cell activator, a skin roughness improving agent, a blood circulation promoter, a skin astringent, an antiseborrheic agent, or the like), vitamins, amino acids, nucleic acids, hormones, and inclusion compounds, as long as the advantageous effects of the present invention are not impaired.

The oily makeup cosmetic of the present invention may comprise a powder, for example. Preferably, the powder may be a powder containing no cation group. Examples of the powder containing no cation group include silicic anhydride (silica), silicone resin powder, PMMA, talc, and mica. The silicic anhydride may have a larger particle size than that of the silica used as the component (d), for example.

The form of the oily makeup cosmetic of the present invention may be, for example, a solid form, a semi-solid form, or a liquid form. Preferably, the oily makeup cosmetic of the present invention is in a liquid form or a semi-solid form, and accordingly advantageous effects of the present invention are markedly exerted. The dosage form of the oily makeup cosmetic of the present invention is preferably oil in which an oil phase is a continuous phase, and accordingly the cosmetic of the present invention may exert an effect of excellent long-lasting makeup properties. For the reason of markedly exerting advantageous effects of the present invention, the content rate of the water in the cosmetic of the present invention is preferably 0.5% or less, more preferably 0.1% or less, and particularly preferably 0% relative to the total mass of the cosmetic of the present invention.

The oily makeup cosmetic of the present invention is colorless. In the present invention, colorless may mean that color development by the component (a) is absent or suppressed. For example, in the present invention, colorless means that the component (a) does not develop a red color or develops a red color at a low degree. The oily makeup cosmetic of the present invention is colorless before application, for example, onto body surface, such as skin and lips, but may develop a color due to the component (a) after application of the cosmetic onto the body surface.

According to an embodiment of the present invention, whether an oily makeup cosmetic is colorless may be determined, for example, by chroma C* as an index. In other words, the oily makeup cosmetic of the present invention preferably has a chroma C* of 5 or less, more preferably 4.25 or less, and even more preferably 3.5 or less. When the chroma C* is within the numerical range, the oily makeup cosmetic of the present invention may be determined to be colorless. The chroma C* is a value determined before application of the cosmetic onto body surface, such as skin and lips, that is, a value determined before color development by the component (a) (or when the color development is suppressed).

The oily makeup cosmetic of the present invention may develop a color due to the component (a) after application of the cosmetic onto body surface, such as skin and lips. In other words, the present invention provides an oily makeup cosmetic that is colorless in appearance but develops a color on application onto body surface, such as skin and lips.

In the present invention, the chroma C* is calculated in accordance with the following calculation formula.

$$C^* = (a^2 + b^2)^{1/2}$$

In the formula, the a value and the b value may be measured as follows: a glass cell (a diameter of 3.5 cm, a depth of 1.2 cm) is completely filled with a sample; and the sample is subjected to measurement with a spectrocolorimeter (SPECTRO COLORMETER SE-2000). The a value and the b value are an a* value and a b* value in the L*a*b* color system (hereinafter also called "Lab color system") (hereinafter, "L* value", "a* value", and "b* value" are also called "L value", "a value", and "b value", respectively).

The oily makeup cosmetic of the present invention preferably has an a value in the Lab color system of 4 or less, more preferably 3 or less, and even more preferably 2 or less. The oily makeup cosmetic of the present invention preferably has an a value in the Lab color system of −5 or more, more preferably −4 or more, and even more preferably −3 or more. The numerical range of the a value of the oily makeup cosmetic of the present invention may be a range defined by values selected from the above upper limits and the above lower limits and may be, for example, −5 to 4, preferably −4 to 3, and more preferably −3 to 2.

The a value is a value measured before application of the cosmetic onto body surface, such as skin and lips, that is, a value of the cosmetic measured before development of a color, specifically a red color, due to the component (a). The a value may be measured by the same method as the measurement method of the a value used for calculation of the chroma C*.

The b value in the Lab color system of the oily makeup cosmetic of the present invention may be set in consideration of the a value so as to achieve the above chroma C*, for example. This is because the chroma C*, the a value, and the b value have the relation expressed by the above calculation formula.

The oily makeup cosmetic of the present invention has a b value in the Lab color system of, for example, 5 or less, preferably 4 or less, and more preferably 3 or less. The oily makeup cosmetic of the present invention has a b value in the Lab color system of, for example, −6 or more, preferably −5 or more, more preferably −4 or more, and even more preferably −3 or more. The numerical range of the b value of the oily makeup cosmetic of the present invention may be a range defined by values selected from the above upper limits and the above lower limits and may be, for example, −6 to 5, preferably −5 to 4, and more preferably −4 to 3.

The b value is a value measured before application of the cosmetic onto body surface, such as skin and lips, that is, a value of the cosmetic measured before development of a red color due to the component (a). The b value may be measured by the same method as the measurement method of the b value used for calculation of the chroma C*.

The L value in the Lab color system of the oily makeup cosmetic of the present invention may be appropriately set by a person skilled in the art. The L value may be, for example, 0 to 100, specifically 1 to 99, more specifically 5 to 95, and even more specifically 10 to 90.

In the present invention, the L value is measured by the same measurement method as the measurement method of the above a value and the b value.

The oily makeup cosmetic of the present invention may develop a color due to the component (a) after application of the cosmetic onto body surface, such as skin and lips. The degree of color development may be evaluated by applying the cosmetic of the present invention before color development, for example, onto a white tissue paper.

The white tissue paper may have a chroma C* of, for example, 0.1 to 5 and specifically 1 to 3. When the oily makeup cosmetic of the present invention is applied onto the white tissue paper, the area with the cosmetic may have a chroma C* of, for example, 20 to 60, specifically 25 to 55, and more specifically 30 to 50.

The white tissue paper may have an a value of, for example, −2 to 2 and specifically −1 to 1. When the oily makeup cosmetic of the present invention is applied onto the white tissue paper, the area with the cosmetic may have an a value of, for example, 15 to 55, specifically 20 to 50, and more specifically 25 to 45.

According to a preferred embodiment of the present invention, the oily makeup cosmetic of the present invention may be colorless and transparent. Whether a cosmetic is transparent may be evaluated by the method described in the following examples. For example, the oily makeup cosmetic of the present invention may have a chroma C* of 5 or less and be transparent.

When the cosmetic of the present invention is transparent, "colorless" may mean the following condition: for example, a polystyrene transparent cell having an optical path length of 1 cm is filled with the cosmetic; then absorbances are measured from 500 to 600 nm with an absorptiometer UV-2500PC manufactured by Shimadzu Corporation in an environment at 25° C.: and the difference between the maximum absorbance and the minimum absorbance in a wavelength region of 500 to 600 nm is 0.5 or less.

According to another preferred embodiment of the present invention, the oily makeup cosmetic of the present invention may be colorless and have an L value of, for example, 45 or more, preferably 50 or more, more preferably 55 or more, and even more preferably 60 or more. For example, the oily makeup cosmetic of the present invention may have a chroma C* of 5 or less and be white.

The oily makeup cosmetic of the present invention may be produced, for example, by the following procedure. First, the component (a) and the component (c) are mixed to disperse the component (a) in the component (c). Next, to the mixture of the component (a) and the component (c) under heat as needed, the component (b) and optional oily components are mixed and/or dispersed. The resulting mixture is homogeneously mixed with optional powders and/or aqueous components, and the mixture is heated to dissolve the components. After dissolution, the mixture is poured in a container or a mold to fill the container or the mold with the mixture. The packed mixture is cooled to give the oily makeup cosmetic of the present invention. The component (d) or the component (e) may be added and mixed, for example, when the component (b) and optional oily components are mixed.

The method for producing the oily makeup cosmetic of the present invention is not limited to the above method. The oily makeup cosmetic of the present invention may be produced by another method known to a person skilled in the art.

The oily makeup cosmetic of the present invention is suitably used as a makeup cosmetic such as a lipstick, a lip gloss, a lip treatment, a lip cream, a lip base for foundation, a lipstick overcoat, a cheek rouge, and an eye shadow. From the viewpoint of markedly achieving advantageous effects of the present invention, the oily makeup cosmetic of the present invention is preferably used as a lip cosmetic such as a lipstick, a lip gloss, a lip treatment, a lip cream, a lip base for foundation, and a lipstick overcoat. In other words, the oily makeup cosmetic of the present invention is preferably a lip cosmetic, that is, a cosmetic intended to be applied onto lips.

The material of the container in which the oily makeup cosmetic of the present invention is stored is preferably such a material as not to cause color development by the component (a). Examples of such a material include, but are not necessarily limited to, polyethylene terephthalate (PET) and polypropylene (PP). In other words, the oily makeup cosmetic of the present invention may be stored in a container made from PET or PP.

EXAMPLES

The present invention will next be described in detail with reference to experimental examples and examples. The scope of the present invention is not necessarily limited to the embodiments shown in these experimental examples and examples.

1. Evaluation of Color Development by Composition Comprising Dye and Oil Agent 1-1. Red No. 218

Experimental Examples 1 to 12 and Comparative Experimental Examples 1 to 3

Red No. 218 as the component (a) and an oil agent were mixed at a mass ratio of 0.1:100 to give a corresponding composition. The formulations of the respective compositions are as shown in Table 1. The color development (or colorlessness) and the time to dyeing (dyeing performance) of each composition were evaluated on the basis of the following criteria. The evaluation results are shown in Table 1. Each composition contained silica dimethyl silylate as a gelling agent for imparting viscosity. Each composition was obtained by homogeneously mixing components as shown in Table 1, with a triple roller.

TABLE 1

(g)

| | Component | Experimental Example | | | | | | | | | | | | Comparative Experimental Example | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 1 | 2 | 3 |
| 1 | R218 *1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| 2 | Silica dimethyl silylate *2 | 1 | 1 | 1 | 1 | 1 | 1 | 1 | 1 | 1 | 1 | 1 | 1 | 1 | 1 | 1 |
| 3 | Polyglyceryl-2 triisostearate (emery type) *3 | 100 | — | — | — | — | — | — | — | — | — | — | — | — | — | — |
| 4 | Triethylhexanoin *4 | — | 100 | — | — | — | — | — | — | — | — | — | — | — | — | — |
| 5 | Tritridecyl trimellitate *5 | — | — | 100 | — | — | — | — | — | — | — | — | — | — | — | — |
| 6 | Dialkyl carbonate (C14, C15) *6 | — | — | — | 100 | — | — | — | — | — | — | — | — | — | — | — |
| 7 | Polyglyceryl-10 decaethylhexanoate | — | — | — | — | 100 | — | — | — | — | — | — | — | — | — | — |
| 8 | Diisostearyl malate *7 | — | — | — | — | — | 100 | — | — | — | — | — | — | — | — | — |
| 9 | Polyglyceryl-2 triisostearate *8 | — | — | — | — | — | — | — | — | — | — | — | — | 100 | — | — |
| 10 | Polyglyceryl-10 decastearate *9 | — | — | — | — | — | — | — | — | — | — | — | — | — | 100 | — |
| 11 | (Vinylpyrrolidone/hexadecene) copolymer *10 | — | — | — | — | — | — | — | — | — | — | — | — | — | — | 100 |
| 12 | Mineral oil *11 | — | — | — | — | — | — | 100 | — | — | — | — | — | — | — | — |
| 13 | Hydrogenated polyisobutene *12 | — | — | — | — | — | — | — | 100 | — | — | — | — | — | — | — |
| 14 | Hydrogenated polyisobutene *13 | — | — | — | — | — | — | — | — | 100 | — | — | — | — | — | — |
| 15 | Methylphenylpolysiloxane *14 | — | — | — | — | — | — | — | — | — | 100 | — | — | — | — | — |
| 16 | Dimethylpolysiloxane *15 | — | — | — | — | — | — | — | — | — | — | 100 | — | — | — | — |
| 17 | Dimethylpolysiloxane *16 | — | — | — | — | — | — | — | — | — | — | — | 100 | — | — | — |

TABLE 1-continued (g)

|  | Component | Expetimental Example | | | | | | | | | | | | Comperative Experimental Example | | |
|---|---|---|---|---|---|---|---|---|---|---|---|---|---|---|---|---|
|  |  | 1 | 2 | 3 | 4 | 5 | 6 | 7 | 8 | 9 | 10 | 11 | 12 | 1 | 2 | 3 |
|  | <<Evaluation items and evaluation results>> | | | | | | | | | | | | | | | |
| a. | Color development | A | A | A | A | A | A | A | A | A | A | A | A | B | B | B |
| b. | Time to dyeing | A | A | A | A | A | B | A | A | B | A | A | B | — | — | — |

*1: TPP Red No. 218 (manufactured by Kishi Kasei Co., Ltd.)
*2: AEROSIL R976S (manufactured by NIPPON AEROSIL CO., LTD.)
*3: Cosmol 43 V (manufactured by Nisshin OilliO)
*4: MYRITOL GTEH (manufactured by BASF)
*5: DOCADIT TM-13N (manufactured by Nisshin OilliO)
*6: LIALCARB SR-1000/R (manufactured by Mitsui Fine Chemical Inc.)
*7: Esterol DISM (manufactured by National Mimatsu Co., Ltd.)
*8: Cosmol 43N (manufactured by Nisshin OilliO)
*9: NIKKOL DECAGLYN 10-ISV (manufactured by Nikko Chemicals)
*10: ANTARON V216 (manufactured by ISP Japan)
*11: KLEAROL WHITE MINERAL OIL (manufactured by SONNEBORN)
*12: Purified polybutene HV-100F (SB) (manufactured by Japan Natural Products)
*13: Nisseki Polybutene HV-1900F (manufactured by JXTG Nippon Oil & Energy Corporation)
*14: Silicone KF-56 (manufactured by Shin-Etsu Chemical Co., Ltd.)
*15: SH200C FLUID 6CS (manufactured by Dow Corning Toray Silicone Co., Ltd.)

(Color Development (or Colorlessness))

Each composition was packed in a polystyrene transparent cell having an optical path length of 1 cm, and then absorbances were measured from 500 to 600 nm with an absorptiometer UV-2500PC manufactured by Shimadzu Corporation in an environment at 25° C. The difference between the maximum absorbance and the minimum absorbance in a wavelength region of 500 to 600 nm was calculated, and the color development was evaluated on the basis of the difference in accordance with the following criteria.
(Criteria): (Evaluation Result)
(Maximum absorbance−minimum absorbance)≤0.2: A (colorless)
(Maximum absorbance−minimum absorbance)≥0.2: B
(Time to Dyeing)

Each composition of Experimental Examples 1 to 12 was applied onto a commercially available tissue paper, and the time from application to red dyeing was measured. On the basis of the measurement result, the dyeing performance of each composition was evaluated in accordance with the following criteria.
(Criteria): (Evaluation Result)
Dyeing within 5 seconds after application: A
Dyeing within 30 seconds but not within 5 seconds after application: B
Dyeing at more than 30 seconds after application or no dyeing: C As apparent from Table 1, the compositions of Experimental Examples 1 to 12 developed no color or were colorless, but the compositions of Comparative Experimental Examples 1 to 3 developed a color when Red No. 218 was mixed with an oil agent.

As shown in Table 1, the compositions of Experimental Examples 1 to 5, 7, 8, 10, and 11 dyed within 5 seconds after application. The compositions of Experimental Examples 6 and 9 dyed within 30 seconds but not within 5 seconds after application.

The compositions of Comparative Experimental Examples 1 to 3 showed no change between the appearance before application and the color after application. The compositions of Comparative Experimental Examples 1 to 3 developed a color immediately after mixing of Red No. 218 and an oil agent, and thus the time to dyeing was not evaluated.

1-2. Red No. 223

Experimental Examples> Experimental Examples 2-1 to 2-12 and Comparative Experimental Examples 2-1 to 2-3

Red No. 223 as the component (a) and an oil agent were mixed at a mass ratio of 0.1:100 to give a corresponding composition. The formulations of the respective compositions are as shown in Table 2. The color development (or colorlessness), the time to dyeing (dyeing performance), and the light stability (color-lasting performance) of each composition were evaluated. The criteria for the color development (or colorlessness) and the time to dyeing (dyeing performance) are as described in <1-1. Red No. 218>. The criteria for the light stability (color-lasting performance) is as described below. The evaluation results are shown in Table 2. Each composition contained silica dimethyl silylate as a gelling agent for imparting viscosity. Each composition was obtained by homogeneously mixing components as shown in Table 2, with a triple roller.

TABLE 2

(g)

| | Component | Experimental Example | | | | | | | | | | | | Comparative Experimental Example | | |
|---|---|---|---|---|---|---|---|---|---|---|---|---|---|---|---|---|
| | | 2-1 | 2-2 | 2-3 | 2-4 | 2-5 | 2-6 | 2-7 | 2-8 | 2-9 | 2-10 | 2-11 | 2-12 | 2-1 | 2-2 | 2-3 |
| 1 | R223 *17 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| 2 | Silica dimethyl silylate *2 | 1 | 1 | 1 | 1 | 1 | 1 | 1 | 1 | 1 | 1 | 1 | 1 | 1 | 1 | 1 |
| 3 | Polyglyceryl-2 triisostearate (emery type) *3 | 100 | — | — | — | — | — | — | — | — | — | — | — | — | — | — |
| 4 | Triethylhexanoin *4 | — | 100 | — | — | — | — | — | — | — | — | — | — | — | — | — |
| 5 | Tritridecyl trimellitate *5 | — | — | 100 | — | — | — | — | — | — | — | — | — | — | — | — |
| 6 | Dialkyl carbonate (C14, C15) *6 | — | — | — | 100 | — | — | — | — | — | — | — | — | — | — | — |
| 7 | Polyglyceryl-10 decaethylhexanoate | — | — | — | — | 100 | — | — | — | — | — | — | — | — | — | — |
| 8 | Diisostearyl malate *7 | — | — | — | — | — | 100 | — | — | — | — | — | — | — | — | — |
| 9 | Polyglyceryl-2 triisostearate *8 | — | — | — | — | — | — | — | — | — | — | — | — | 100 | — | — |
| 10 | Polyglyceryl-10 decastearate *9 | — | — | — | — | — | — | — | — | — | — | — | — | — | 100 | — |
| 11 | (Vinylpyrrolidone/ hexadecene) copolymer *10 | — | — | — | — | — | — | — | — | — | — | — | — | — | — | 100 |
| 12 | Mineral oil *11 | — | — | — | — | — | — | 100 | — | — | — | — | — | — | — | — |
| 13 | Hydrogenated polyisobutene *12 | — | — | — | — | — | — | — | 100 | — | — | — | — | — | — | — |
| 14 | Hydrogenated polyisobutene *13 | — | — | — | — | — | — | — | — | 100 | — | — | — | — | — | — |
| 15 | Methylphenylpolysiloxane *14 | — | — | — | — | — | — | — | — | — | 100 | — | — | — | — | — |
| 16 | Dimethylpolysiloxane *15 | — | — | — | — | — | — | — | — | — | — | 100 | — | — | — | — |
| 17 | Dimethylpolysiloxane *16 | — | — | — | — | — | — | — | — | — | — | — | 100 | — | — | — |
| | <<Evaluation items and evaluation results>> | | | | | | | | | | | | | | | |
| a. | Color development | A | A | A | A | A | A | A | A | A | A | A | A | B | B | B |
| b. | Time to dyeing | B | B | B | B | B | B | B | B | C | B | B | C | — | — | — |
| c. | Light stability (time to dyeing after application of FL for 1 week) | C | B | B | B | B | B | B | C | C | B | B | C | — | — | — |

*17: TPP Red No. 223 (manufactured by Kishi Kasei Co., Ltd.)
*2: AEROSIL R976S (manufactured by NIPPON AEROSIL CO., LTD.)
*3: Cosmol 43 V (manufactured by Nisshin OilliO)
*4: MYRITOL GTEH (manufactured by BASF)
*5: DOCADIT TM-13N (manufactured by Nisshin OilliO)
*6: LIALCARB SR-1000/R (manufactured by Mitsui Fine Chemical Inc.)
*7: Esterol DISM (manufactured by National Mimatsu Co., Ltd.)
*8: Cosmol 43N (manufactured by Nisshin OilliO)
*9: NIKKOL DECAGLYN 10-ISV (manufactured by Nikko Chemicals)
*10: ANTARON V216 (manufactured by ISP Japan)
*11: KLEAROL WHITE MINERAL OIL (manufactured by SONNEBORN)
*12: Purified polybutene HV-100F (SB) (manufactured by Japan Natural Products)
*13: Nisseki Polybutene HV-1900F (manufactured by JXTG Nippon Oil & Energy Corporation)
*14: Silicone KF-56 (manufactured by Shin-Etsu Chemical Co., Ltd.)
*15: SH200C FLUID 6CS (manufactured by Dow Corning Toray Silicone Co., Ltd.)
*16: KF-96H-100,000CS (manufactured by Shin-Etsu Chemical Co., Ltd.)

(Light Stability) Evaluation of Color-Lasting Performance

Each composition of Experimental Examples 2-1 to 2-12 was packed in a transparent container (PET) and was allowed to stand in an environment with white fluorescent light at 8,000 to 10,000 lux for a week. After the standing, each composition was applied onto a commercially available tissue paper. The time immediately after application to red dyeing was measured, and the light stability of each composition was evaluated in accordance with the following criteria.

(Criteria): (Evaluation)

Dyeing within 5 seconds after application: A

Dyeing within 30 seconds but not within 5 seconds after application: B

Dyeing at more than 30 seconds after application or no dyeing: C

As apparent from Table 2, the compositions of Experimental Examples 2-1 to 2-12 developed no color (were colorless), but the compositions of Comparative Experimental Examples 2-1 to 2-3 developed a color when Red No. 223 and an oil agent were mixed.

The compositions of Experimental Examples 2-1 to 2-8, 2-10, and 2-11 dyed within 30 seconds but not within 5 seconds of after application. The compositions of Experimental Examples 2-9 and 2-12 developed a color at more than 30 seconds after application. Hence, the oil agents contained in the compositions of Experimental Examples 2-1 to 2-8, 2-10, and 2-11 may give excellent dyeing performance to oily makeup cosmetics.

The compositions of Experimental Examples 2-2 to 2-7, 2-10, and 2-11 dyed within 30 seconds but not within 5 seconds after application, even after photoirradiation for a week. The compositions of Experimental Examples 2-1, 2-8, 2-9, and 2-12 developed a color at more than 30 seconds after application. Hence, the oil agents contained in the compositions of Experimental Examples 2-2 to 2-7, 2-10, and 2-11 may give excellent light stability to oily makeup cosmetics.

The compositions of Comparative Experimental Examples 2-1 to 2-3 showed no change between the appearance before application and the color after application. The compositions of Comparative Experimental Example 2-1 to 2-3 developed a color immediately after mixing of Red No. 223 and an oil agent, and thus neither the time to dyeing nor the light stability was evaluated.

When the compositions of Experimental Examples 1 to 12 are compared with the compositions of Experimental Examples 2-1 to 2-12, the compositions of Experimental Examples 1 to 12 are likely to have more excellent dyeing performance. Hence, an oily makeup cosmetic containing Red No. 218 obtains more excellent dyeing performance as compared with that containing Red No. 223.

2. Oily Lip Cosmetic Containing Red No. 218

Examples 1 to 16 and Comparative Examples 1 to 5

Oily lip cosmetics having formulations shown in Table 3 were produced in accordance with the following production method. The color development (or colorlessness), the time to dyeing on application, light stability and high-temperature stability in a certain environment of each of the resulting oily lip cosmetics, and transparency of each cosmetic in appearance were evaluated in accordance with the following evaluation methods. The evaluation results are shown in Table 3.

TABLE 3

(%)

| | Component + B2:C40 | Example 1 | 2 | 3 | 4 | 5 | 6 | 7 | 8 | 9 | 10 | 11 | 12 |
|---|---|---|---|---|---|---|---|---|---|---|---|---|---|
| 1 | R218 *1 | 0.03 | 0.01 | 1 | 0.03 | 0.03 | 0.03 | 0.03 | 0.03 | 0.03 | 0.03 | 0.03 | 0.03 |
| 2 | R223 *17 | — | — | — | — | — | — | — | — | — | — | — | — |
| 3 | Silica dimethyl silylate *2 | 0.3 | 0.3 | 0.3 | 0.3 | 0.3 | 0.3 | 0.3 | 0.3 | 0.3 | 0.3 | 0.3 | 0.3 |
| 4 | (Acrylic acid/alkyl (C10-30) acrylate) copolymer *18 | 0.06 | 0.1 | 0.5 | — | 0.06 | 0.06 | 0.06 | 0.06 | 0.06 | 0.06 | 0.06 | 0.06 |
| 5 | Carbomer *19 | — | — | — | 0.06 | — | — | — | — | — | — | — | — |
| 6 | Polyglyceryl-2 triisostearate (emery type) *3 | Remainder | Remainder | Remainder | Remainder | Remainder | Remainder | Remainder | Remainder | Remainder | Remainder | Remainder | Remainder |
| 7 | Diisostearyl malate *7 | 10 | 10 | 10 | 10 | 10 | 10 | 10 | 10 | 10 | 10 | 10 | — |
| 8 | Tritridecyl trimellitate *5 | 30 | 30 | 30 | — | — | — | — | 30 | 30 | 30 | 30 | — |
| 9 | Triethylhexanoin *4 | — | — | — | 30 | 30 | — | — | — | — | — | — | — |
| 10 | Dialkyl carbonate (C14, C15) *6 | — | — | — | — | — | 30 | — | — | — | — | — | — |
| 11 | Polyglyceryl-10 decaethylhexanoate | — | — | — | — | — | — | 30 | — | — | — | — | — |
| 12 | Polyglyceryl-2 triisostearate *8 | — | — | — | — | — | — | — | 0.1 | — | — | — | — |
| 13 | Polyglyceryl-10 decastearate *9 | — | — | — | — | — | — | — | — | 0.1 | — | — | — |
| 14 | (Vinylpyrrolidone/hexadecene) copolymer *10 | — | — | — | — | — | — | — | — | — | 0.1 | — | — |
| 15 | Mineral oil *11 | 12 | 12 | 12 | 12 | 12 | 12 | 12 | 12 | 12 | 12 | 12 | — |
| 16 | Hydrogenated polyisobutene *12 | 20 | 20 | 20 | 20 | 20 | 20 | 20 | 20 | 20 | 20 | 20 | — |
| 17 | Hydrogenated polyisobutene *13 | 18 | 18 | 18 | 18 | 18 | 18 | 18 | 18 | 18 | 18 | 18 | 60 |
| 18 | Methylphenylpolysiloxane *14 | — | — | — | — | — | — | — | — | — | — | — | — |
| 19 | Dimethylpolysiloxane *16 | — | — | — | — | — | — | — | — | — | — | — | — |
| 20 | Dextrin palmitate *20 | 4 | 4 | 4 | 4 | 4 | 4 | 4 | 4 | 4 | 4 | 4 | 4 |
| 21 | Silica dimethyl silylate *2 | 1.5 | 1.5 | 1.5 | 1.5 | 1.5 | 1.5 | 1.5 | 1.5 | 1.5 | 1.5 | 1.5 | 1.5 |
| 22 | Titanium oxide-coated glass powder *21 | — | — | — | — | — | — | — | — | — | — | — | — |
| 23 | Dipropylene glycol | — | — | — | — | — | — | — | — | — | — | 0.5 | — |
| | Component (a)/component (c) | 0.5 | 0.1 | 2 | 0.5 | 0.5 | 0.5 | 0.5 | 0.5 | 0.5 | 0.5 | 0.5 | 0.5 |
| | Additional liquid component other than component (b) | 0 | 0 | 0 | 0 | 0 | 0 | 0 | 0.1 | 0.1 | 0.1 | 0.5 | 0 |
| | Dynamic viscosity of cosmetic | 2 | 2 | 2 | 2 | 2 | 2 | 2 | 2 | 2 | 2 | 2 | 2 |

\<Evaluation items and evaluation results\>

| | | | | | | | | | | | | | |
|---|---|---|---|---|---|---|---|---|---|---|---|---|---|
| a. | Color development | A | A | A | A | A | A | A | A | A | A | A | A |
| b. | Time to dyeing | A | A | A | A | A | A | A | A | A | A | A | B |
| c. | Light stability (time to dyeing after application of FL for 1 week) | A | A | A | B | A | A | A | A | A | A | A | A |

TABLE 3-continued

| | | | | | | | | | | | | |
|---|---|---|---|---|---|---|---|---|---|---|---|---|
| d | High-temperature stability (color development after standing at 50° C. for 1 week) | A | A | A | A | A | A | A | A | A | A | A |
| e | Transparency | A | A | A | A | A | A | A | A | A | A | A |

(%)

| | | Example | | | | Comparative Example | | | | |
|---|---|---|---|---|---|---|---|---|---|---|
| | Component + B2:C40 | 13 | 14 | 15 | 16 | 1 | 2 | 3 | 4 | 5 |
| 1 | R218 *1 | 0.03 | 0.03 | — | 0.03 | 0.03 | 0.03 | 0.03 | 0.03 | 0.03 |
| 2 | R223 *17 | — | — | 0.03 | — | — | — | — | — | — |
| 3 | Silica dimethyl silylate *2 | 0.3 | 0.3 | 0.3 | 0.3 | 0.3 | 0.3 | 0.3 | 0.3 | 0.3 |
| 4 | (Acrylic acid/alkyl (C10-30) acrylate) copolymer *18 | 0.06 | 0.06 | 0.06 | — | 0.06 | 0.06 | 0.06 | 0.06 | 0.06 |
| 5 | Carbomer *19 | — | — | — | — | — | — | — | — | — |
| 6 | Polyglyceryl-2 triisostearate (emery type) *3 | Remainder | Remainder | Remainder | Remainder | Remainder | Remainder | Remainder | Remainder | Remainder |
| 7 | Diisostearyl malate *7 | — | 10 | 10 | 10 | 10 | — | — | — | 10 |
| 8 | Tritridecyl trimellitate *5 | — | 30 | 30 | 30 | 30 | — | — | — | 30 |
| 9 | Triethylhexanoin *4 | — | — | — | — | — | — | — | — | — |
| 10 | Dialkyl carbonate (C14, C15) *6 | — | — | — | — | — | — | — | — | — |
| 11 | Polyglyceryl-10 decaethylhexanoate | — | — | — | — | — | — | — | — | — |
| 12 | Polyglyceryl-2 triisostearate *8 | — | — | — | — | — | — | — | 30 | — |
| 13 | Polyglyceryl-10 decastearate *9 | — | — | — | — | — | 30 | — | — | — |
| 14 | (Vinylpyrrolidone/hexadecene) copolymer *10 | — | — | — | — | 0.7 | — | 30 | 30 | — |
| 15 | Mineral oil *11 | — | 12 | 12 | 12 | 12 | 12 | 12 | — | 12 |
| 16 | Hydrogenated polyisobutene *12 | — | 20 | 20 | 20 | 20 | 20 | 20 | — | 20 |
| 17 | Hydrogenated polyisobutene *13 | — | 18 | 18 | 18 | 18 | 18 | 18 | — | 18 |
| 18 | Methylphenylpolysiloxane *14 | 15 | — | — | — | — | — | — | — | — |
| 19 | Dimethylpolysiloxane *16 | 30 | — | — | — | — | — | — | — | — |
| 20 | Dextrin palmitate *20 | 4 | — | 4 | 4 | 4 | 4 | 4 | 4 | 4 |
| 21 | Silica dimethyl silylate *2 | 1.5 | 3 | 1.5 | 1.5 | 1.5 | 1.5 | 1.5 | 1.5 | 1.5 |
| 22 | Titanium oxide-coated glass powder *21 | — | 1 | — | — | — | — | — | — | — |
| 23 | Dipropylene glycol | — | — | — | — | — | — | — | — | 1 |
| | Component (a)/component (c) | 0.5 | 0.5 | 0.5 | — | 0.5 | 0.5 | 0.5 | 0.5 | 0.5 |
| | Additional liquid component other than component (b) | 0.5 | 0 | 0 | 0 | 0.7 | 30 | 30 | 60 | 1 |
| | Dynamic viscosity of cosmetic | 2 | 2 | 2 | 2 | 2 | 2 | 2 | 2 | 2 |
| | <Evaluation items and evaluation results> | | | | | | | | | |
| a. | Color development | A | A | A | A | B | B | B | B | B |
| b. | Time to dyeing | B | A | A | A | — | — | — | — | — |
| c. | Light stability (time to dyeing after application of FL for 1 week) | A | A | C | A | — | — | — | — | — |
| d | High-temperature stability (color development after standing at 50° C. for 1 week) | A | A | A | B | — | — | — | — | — |
| e | Transparency | A | A | B | A | — | — | — | — | — |

*17: TPP Red No. 223 (manufactured by Kishi Kasei Co., Ltd.)
*18: PEMULEN TR2 (manufactured by LUBRIZOL ADVANCED MATERIALS)
*19: Carbopol 980 (manufactured by LUBRIZOL ADVANCED MATERIALS)
*20: Rheopearl KL2 (manufactured by Chiba Four Milling Co., Ltd.)
*21: Metashine 1080RR (manufactured by Nippon Sheet Glass Co., Ltd.)

(Production method): Cosmetics of Examples 1 to 16 and Comparative Examples 1 to 5
A. Components (1) to (5) are homogeneously mixed.
B. A and components (6) to (21) and (23) are homogeneously mixed with a triple roller.
C. B and a component (22) are homogeneously mixed.
D. C is heated to 100° C. and is packed in a container, giving an oily lip cosmetic.
(Color development): Evaluation of colorlessness Each cosmetic was packed in a polystyrene transparent cell having an optical path length of 1 cm, and then absorbances were measured from 500 to 600 nm with an absorptiometer UV-2500PC manufactured by Shimadzu Corporation in an environment at 25° C. The difference between the maximum absorbance and the minimum absorbance in a wavelength region of 500 to 600 nm was calculated, and the color development was evaluated on the basis of the difference in accordance with the following criteria.
(Criteria): (Evaluation)
(Maximum absorbance−minimum absorbance)≤0.5: A (colorless)
(Maximum absorbance−minimum absorbance)≥0.5: B
(Time to dyeing): Evaluation of dyeing performance Each cosmetic was applied onto a commercially available tissue paper, and the time from application to red dyeing was measured. On the basis of the measurement result, the dyeing performance of each composition was evaluated in accordance with the following criteria.
(Criteria): (Evaluation)
Dyeing within 5 seconds after application: A
Dyeing within 30 seconds but not within 5 seconds after application: B
Dyeing at more than 30 seconds after application or no dyeing: C
(Light stability): Evaluation of color-lasting performance Each cosmetic was packed in a transparent container (PET) and was allowed to stand in an environment with white fluorescent light at 8,000 to 10,000 lux for a week. After the standing, each cosmetic was applied onto a commercially available tissue paper. The time immediately after application to red dyeing was measured, and the light stability of each cosmetic was evaluated in accordance with the following criteria.
(Criteria): (Evaluation)
Dyeing within 5 seconds after application: A
Dyeing within 30 seconds but not within 5 seconds after application: B
Dyeing at more than 30 seconds after application or no dyeing: C
(High-temperature stability): Evaluation of discoloration Each cosmetic was allowed to stand in a constant temperature chamber at 50° C. for a week. After the standing, each cosmetic was packed in a polystyrene transparent cell having an optical path length of 1 cm, and then absorbances were measured from 500 to 600 nm with an absorptiometer UV-2500PC manufactured by Shimadzu Corporation in an environment at 25° C. The difference between the maximum absorbance and the minimum absorbance in a wavelength region of 500 to 600 nm was calculated, and the high-temperature stability was evaluated on the basis of the difference in accordance with the following criteria.
(Criteria): (Evaluation)
(Maximum absorbance−minimum absorbance)≤0.5: A (colorless)
(Maximum absorbance−minimum absorbance)≥0.5: B
(Transparency)

Each cosmetic was applied onto a transparent glass plate to form a coating having a thickness of 500 μm. Under the glass plate, a paper with a lattice pattern was placed, and whether the clear lattice pattern was visually observed was evaluated in accordance with the following criteria.
(Criteria): (Evaluation)
The clear lattice pattern is observable: A
The clear lattice pattern is unobservable: B
(Dynamic viscosity at 25° C.)

The dynamic viscosity of each cosmetic was determined by ASTM D445 measurement method at 25° C. On the basis of the measurement result, each cosmetic was classified in accordance with the following standards.
(Standard): (Classification)
The dynamic viscosity is not less than 20,000 cs: 3
The dynamic viscosity is not less than 10,000 cs and less than 20,000 cs: 2
The dynamic viscosity is less than 10,000 cs: 1

As apparent from the results in Table 3, each oily lip cosmetic of Examples 1 to 16 was colorless in appearance but developed a color on application. In contrast, each oily lip cosmetic of Comparative Examples 1 to 5 developed a color before application.

Figure 1:
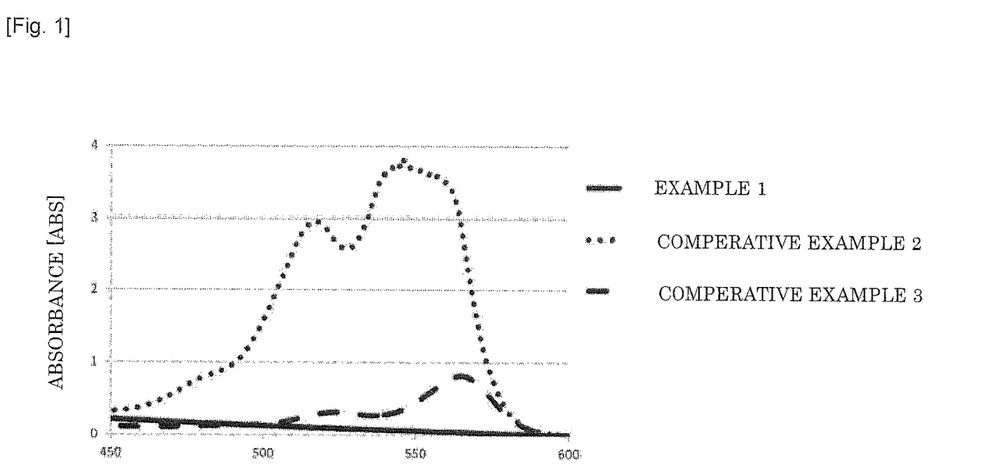
FIG. 1 is a graph showing measurement results of absorbances of cosmetics of Example 1 and Comparative Examples 2 and 3.

FIG. 1 shows the measurement results of the absorbances of the oily lip cosmetics of Example 1 and Comparative Examples 2 and 3. FIG. 1 also reveals that the oily lip cosmetics of Comparative Examples 2 and 3 developed a color before application but the oily lip cosmetic of Example 1 developed no color before application.

Examples 1 to 15 had excellent high-temperature stability. In contrast, Example 16 was inferior in high-temperature stability to Examples 1 to 15, and the cosmetic developed a red color with time.

Examples 1 to 14 and Example 16 had excellent transparency. In contrast, Example 15 was inferior in transparency to the other Examples.

Examples 1 to 14 and Example 16 had excellent light stability. In contrast, Example 15 containing Red No. 223 in place of Red No. 218 was inferior in light stability to the other Examples.

As described above, each oily lip cosmetic of Examples 1 to 14 was colorless in appearance, but developed a color on application, had excellent light stability and high-temperature stability, and also had excellent transparency.

Example 15 containing Red No. 223 in place of Red No. 218 was inferior in light stability to the other Examples. This reveals that use of Red No. 218 provides an effect of yielding a cosmetic having more excellent light stability than use of Red No. 223.

Example 16 containing no component (c) was inferior in high temperature stability to the other Examples, and the cosmetic developed a red color with time. This reveals that use of component (c) provides an effect of excellent high-temperature stability.

Comparative Examples 1 to 5 that contained an additional liquid component other than the component (b) at more than 0.5% developed a red color in appearance and had no change in color before and after application.

3. Oily Lip Cosmetic Containing Red No. 223

Examples 2-1 to 2-16 and Comparative Examples 2-1 to 2-5

Oily lip cosmetics having formulations shown in Table 4 were produced in accordance with the following production method. The color development (or colorlessness), the time to dyeing on application, light stability and high-temperature stability in a certain environment of each of the resulting oily lip cosmetics, and transparency of each cosmetic in appearance were evaluated in accordance with the evaluation methods described in <2. Oily lip cosmetic containing Red No. 218>. The evaluation results are shown in Table 4.

TABLE 4

(%)

| | Component | Example 2-1 | 2-2 | 2-3 | 2-4 | 2-5 | 2-6 | 2-7 | 2-8 | 2-9 | 2-10 | 2-11 | 2-12 |
|---|---|---|---|---|---|---|---|---|---|---|---|---|---|
| 1 | R223 *1 | 0.03 | 0.01 | 1 | 0.03 | 0.03 | 0.03 | 0.03 | 0.03 | 0.03 | 0.03 | 0.03 | 0.03 |
| 2 | Silica dimethyl silylate *2 | 0.3 | 0.3 | 0.3 | 0.3 | 0.3 | 0.3 | 0.3 | 0.3 | 0.3 | 0.3 | 0.3 | 0.3 |
| 3 | (Acrylic acid/alkyl (C10-30) acrylate) copolymer *18 | 0.06 | 0.1 | 0.5 | — | 0.06 | 0.06 | 0.06 | 0.06 | 0.06 | 0.06 | 0.06 | 0.06 |
| 4 | Carbomer *19 | — | — | — | 0.06 | — | — | — | — | — | — | — | — |
| 5 | Diisostearyl malate *7 | Remainder | Remainder | Remainder | Remainder | Remainder | Remainder | Remainder | Remainder | Remainder | Remainder | Remainder | Remainder |
| 6 | Tritridecyl trimellitate *5 | 30 | 30 | 30 | 30 | — | — | — | — | 30 | 30 | 30 | 30 |
| 7 | Triethylhexanoin *4 | — | — | — | — | 30 | — | — | — | — | — | — | — |
| 8 | Dialkyl carbonate (C14, C15) *6 | — | — | — | — | — | 30 | — | — | — | — | — | — |
| 9 | Polyglyceryl-10 decaethylhexanoate | — | — | — | — | — | — | 30 | — | — | — | — | — |
| 10 | Polyglyceryl-2 triisostearate (emery type) *3 | — | — | — | — | — | — | — | 30 | — | — | — | — |
| 11 | Polyglyceryl-2 triisostearate *8 | — | — | — | — | — | — | — | — | 0.1 | — | — | — |
| 12 | Polyglyceryl-10 decastearate *9 | — | — | — | — | — | — | — | — | — | 0.1 | — | |
| 13 | (Vinylpyrrolidone/hexadecene) copolymer *10 | — | — | — | — | — | — | — | — | — | — | 0.1 | — |
| 14 | Mineral oil *11 | 12 | 12 | 12 | 12 | 12 | 12 | 12 | 12 | 12 | 12 | 12 | 12 |
| 15 | Hydrogenated polyisobutene *12 | — | — | — | — | — | — | — | — | — | — | — | — |
| 16 | Hydrogenated polyisobutene *13 | — | — | — | — | — | — | — | — | — | — | — | — |
| 17 | Methylphenylpolysiloxane *14 | 8 | 8 | 8 | 8 | 8 | 8 | 8 | 8 | 8 | 8 | 8 | 8 |
| 18 | Dimethylpolysiloxane *16 | — | — | — | — | — | — | — | — | — | — | — | — |
| 19 | Dextrin palmitate *20 | 4 | 4 | 4 | 4 | 4 | 4 | 4 | 4 | 4 | 4 | 4 | 4 |
| 20 | Silica dimethyl silylate *2 | 1.5 | 1.5 | 1.5 | 1.5 | 1.5 | 1.5 | 1.5 | 1.5 | 1.5 | 1.5 | 1.5 | 1.5 |
| 21 | Titanium oxide-coated glass powder *21 | — | — | — | — | — | — | — | — | — | — | — | — |
| 22 | Dipropylene glycol | — | — | — | — | — | — | — | — | — | — | — | 0.5 |
| | Component (a)/component (c) | 0.5 | 0.1 | 2 | 0.5 | 0.5 | 0.5 | 0.5 | 0.5 | 0.5 | 0.5 | 0.5 | 0.5 |
| | Additional liquid component other than component (b) | 0 | 0 | 0 | 0 | 0 | 0 | 0 | 0 | 0.1 | 0.1 | 0.1 | 0.5 |
| | Dynamic viscosity of cosmetic | 2 | 2 | 2 | 2 | 2 | 2 | 2 | 2 | 2 | 2 | 2 | 2 |

<Evaluation items and evaluation results>

| | | 2-1 | 2-2 | 2-3 | 2-4 | 2-5 | 2-6 | 2-7 | 2-8 | 2-9 | 2-10 | 2-11 | 2-12 |
|---|---|---|---|---|---|---|---|---|---|---|---|---|---|
| a. | Color development | A | A | A | A | A | A | A | A | A | A | A | A |
| b. | Time to dyeing | A | A | A | A | A | A | A | A | A | A | A | A |
| c. | Light stability (time to dyeing after application of FL for 1 week) | A | A | A | A | A | A | A | B | A | A | A | A |
| d | High-temperature stability (color development after standing at 50° C. for 1 week) | A | A | A | A | A | A | A | A | A | A | A | A |
| e | Transparency | A | A | A | A | A | A | A | A | A | A | A | A |

(%)

| | Component | Example 2-13 | 2-14 | 2-15 | 2-16 | Comparative Experimental Example 2-1 | 2-2 | 2-3 | 2-4 | 2-5 |
|---|---|---|---|---|---|---|---|---|---|---|
| 1 | R223 *1 | 0.03 | 0.03 | 0.03 | 0.03 | 0.03 | 0.03 | 0.03 | 0.03 | 0.03 |
| 2 | Silica dimethyl silylate *2 | 0.3 | 0.3 | 0.3 | 0.3 | 0.3 | 0.3 | 0.3 | 0.3 | 0.3 |
| 3 | (Acrylic acid/alkyl (C10-30) acrylate) copolymer *18 | 0.06 | 0.06 | 0.06 | — | 0.06 | 0.06 | 0.06 | 0.06 | 0.06 |
| 4 | Carbomer *19 | — | — | — | — | — | — | — | — | — |
| 5 | Diisostearyl malate *7 | Remainder | Remainder | Remainder | Remainder | Remainder | Remainder | Remainder | Remainder | Remainder |
| 6 | Tritridecyl trimellitate *5 | — | — | 30 | 30 | 30 | — | — | — | 30 |
| 7 | Triethylhexanoin *4 | — | — | — | — | — | — | — | — | — |
| 8 | Dialkyl carbonate (C14, C15) *6 | — | — | — | — | — | — | — | — | — |

TABLE 4-continued

| # | Component | | | | | | | | | |
|---|---|---|---|---|---|---|---|---|---|---|
| 9 | Polyglyceryl-10 decaethylhexanoate | — | — | — | — | — | — | — | — | — |
| 10 | Polyglyceryl-2 triisostearate (emery type) *3 | — | — | — | — | — | — | — | — | — |
| 11 | Polyglyceryl-2 triisostearate *8 | — | — | — | — | — | — | — | 30 | — |
| 12 | Polyglyceryl-10 decastearate *9 | — | — | — | — | 30 | — | — | — | — |
| 13 | (Vinylpyrrolidone/hexadecene) copolymer *10 | — | — | — | — | 0.7 | — | 30 | 30 | — |
| 14 | Mineral oil *11 | — | — | 12 | 12 | 12 | 12 | 12 | — | 12 |
| 15 | Hydrogenated polyisobutene *12 | 10 | — | — | — | — | — | — | — | — |
| 16 | Hydrogenated polyisobutene *13 | 20 | — | — | — | — | — | — | — | — |
| 17 | Methylphenylpolysiloxane *14 | 8 | 8 | 8 | 8 | 8 | 8 | 8 | — | 8 |
| 18 | Dimethylpolysiloxane *16 | — | 30 | — | — | — | — | — | — | — |
| 19 | Dextrin palmitate *20 | 4 | 4 | — | 4 | 4 | 4 | 4 | 4 | 4 |
| 20 | Silica dimethyl silylate *2 | 1.5 | 1.5 | 3 | 1.5 | 1.5 | 1.5 | 1.5 | 1.5 | 1.5 |
| 21 | Titanium oxide-coated glass powder *21 | — | — | 1 | — | — | — | — | — | — |
| 22 | Dipropylene glycol | — | — | — | — | — | — | — | — | 1 |
| | Component (a)/component (c) | 0.5 | 0.5 | 0.5 | — | 0.5 | 0.5 | 0.5 | 0.5 | 0.5 |
| | Additional liquid component other than component (b) | 0 | 0 | 0 | 0 | 0.7 | 30 | 30 | 60 | 1 |
| | Dynamic viscosity of cosmetic | 2 | 3 | 2 | 2 | 2 | 2 | 2 | 2 | 2 |
| | <Evaluation items and evaluation results> | | | | | | | | | |
| a. | Color development | A | A | A | A | B | B | B | B | B |
| b. | Time to dyeing | B | B | A | A | — | — | — | — | — |
| c. | Light stability (time to dyeing after application of FL for 1 week) | B | B | A | A | — | — | — | — | — |
| d | High-temperature stability (color development after standing at 50° C. for 1 week) | A | A | A | B | — | — | — | — | — |
| e | Transparency | A | A | A | A | — | — | — | — | — |

*18: PEMULEN TR2 (manufactured by LUBRIZOL ADVANCED MATERIALS)
*19: Carbopol 980 (manufactured by LUBRIZOL ADVANCED MATERIALS)
*20: Rheopearl KL2 (manufactured by Chiba Four Milling Co., Ltd.)
*21: Metashine 1080RR (manufactured by Nippon Sheet Glass Co., Ltd.)

As apparent from the results in Table 4, each oily lip cosmetic of Examples 2-1 to 2-16 was colorless in appearance but developed a color on application. In contrast, each oily lip cosmetic of Comparative Examples 2-1 to 2-5 developed a color before application.

Example 2-1 to 2-15 had excellent high-temperature stability. In contrast, Example 2-16 was inferior in high-temperature stability to Examples 2-1 to 2-15, and the cosmetic developed a red color with time.

Examples 2-1 to 2-16 each had excellent transparency.

Example 2-1 to 2-7, 2-9 to 2-12, 2-15, and 2-16 had excellent light stability. In contrast, Example 2-8, 2-13, and 2-14 were inferior in light stability to the other Examples.

As described above, the oily lip cosmetics of Examples 2-1 to 2-15 were colorless in appearance but developed a color on application, had excellent light stability and high-temperature stability, and also had excellent transparency.

Example 2-16 containing no component (c) was inferior in high-temperature stability to Examples 2-1 to 2-15, and the cosmetic developed a red color with time. This reveals that use of component (c) provides an effect of excellent high-temperature stability.

Comparative Examples 2-1 to 2-5 that contained an additional liquid component other than the component (b) at more than 0.5% developed a color in appearance and had no change in color before and after application.

4. Measurement Result of Lab Value

The L value, the a value, and the b value in the Lab color system of each oily lip cosmetic of Examples 1 and 10, Comparative Example 3, Examples 2-1 and 2-11, and Comparative Example 2-2 produced in <2. Oily lip cosmetic containing Red No. 218> and <3. Oily lip cosmetic containing Red No. 223> were measured. On the basis of the a value and the b value as the measurement results, the chroma C* was calculated.

The measurement was performed by using each cosmetic packed in a glass cell (a diameter of 3.5 cm, a depth of 1.2 cm) with a spectrocolorimeter (SPECTRO COLORMETER SE-2000).

The evaluation results are shown in Table 5. The color development in Table 5 shows the results described in <2. Oily lip cosmetic containing Red No. 218> and <3. Oily lip cosmetic containing Red No. 223>.

TABLE 5

|  | R218 | | | R223 | | |
| --- | --- | --- | --- | --- | --- | --- |
|  | Example1 | Example10 | Comparative Experimental Example3 | Example2-1 | Example2-11 | Comparative Experimental Example2-2 |
| L value | 15.56 | 13.36 | 23.74 | 18.89 | 18.59 | 21.15 |
| a value | 0.19 | 0.18 | 17.73 | 0.32 | 0.44 | 1.82 |
| b value | −3.19 | −3.42 | 12.74 | −0.81 | 3.17 | 10.21 |
| Chroma: $(a^2 + b^2)^{1/2}$ | 3.20 | 3.42 | 21.83 | 0.87 | 3.20 | 10.37 |
| a. Color development | A | A | B | A | A | B |

As shown in Table 5, each cosmetic of Examples 1 and 10 and Examples 2-1 and 2-11 had a chroma C* of 5 or less. In other words, these cosmetics were each colorless.

Each cosmetic of Examples 1 and 10 and Examples 2-1 and 2-11 had an a value of 4 or less. In other words, in each of these cosmetics, red color development was suppressed.

5. Degree of Color Development

The oily lip cosmetic of Example 1 was applied onto a white tissue paper, and then the Lab value of the developed color was measured. On the basis of the measurement result, the chroma was calculated. To evaluate the degree of color development, the Lab value and the chroma of the tissue paper before application were similarly determined. These Lab values and chromas are shown in Table 6.

TABLE 6

|  | Before application | After application |
| --- | --- | --- |
| L value | 88.85 | 61.95 |
| a value | −0.8 | 35.12 |
| b value | 1.27 | −15.5 |
| Chroma: $(a^2 + b^2)^{1/2}$ | 1.50 | 38.39 |

As shown in Table 6, the chroma before application was 1.50, and the chroma after application was 38.39. As shown in Table 6, the a value before application was −0.8, and the a value after application was 35.12. In other words, by applying the cosmetic onto a tissue paper, the chroma and the a value of the applied area increased, that is, the color due to Red No. 218 in the cosmetic was developed.

6. Color Development of Each Dosage Form

It was ascertained by the following experiments that suppression of red color development by a combination of a red dye and a particular oil agent is achieved not only by the compositions in a gel dosage form adopted in <1. Evaluation of color development by composition comprising dye and oil agent> but also by compositions in other dosage forms.

Compositions 1 to 6 having formulations as shown in Table 7 were produced. The L value, the a value, and the b value in the Lab color system of each composition were measured. On the basis of the a value and the b value as the measurement results, the chroma C* was calculated.

The measurement was performed by using each cosmetic packed in a glass cell (a diameter of 3.5 cm, a depth of 1.2 cm) with a spectrocolorimeter (SPECTRO COLORMETER SE-2000).

The evaluation results are also shown in Table 7. The color development in Table 7 was evaluated in accordance with the criteria as described in <1. Evaluation of color development by composition comprising dye and oil agent>.

Figure 2:
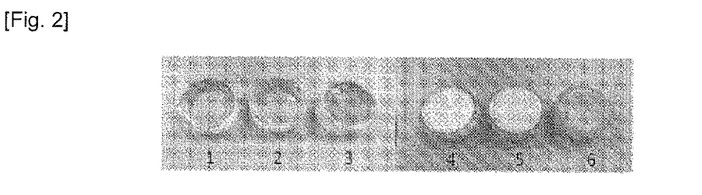
FIG. 2 are photographs of compositions 1 to 6.

Photographs of the compositions 1 to 6 are shown in FIG. 2.

TABLE 7

| | (unit: % by mass) | | | | | |
| --- | --- | --- | --- | --- | --- | --- |
| Composition No. | 1 | 2 | 3 | 4 | 5 | 6 |
| Dextrin palmitate *20 | 5 | 5 | 5 | — | — | — |
| Ethylene/propylene) copolymer (hydrocarbon solid oil) | — | — | — | 8 | 8 | 8 |
| Diisostearyl malate *8 | 94.9 | 94.4 | 64.9 | 91.9 | 91.4 | 61.9 |
| R218 *1 | 0.1 | 0.1 | 0.1 | 0.1 | 0.1 | 0.1 |
| (Vinyl-pyrrolidone/hexadecene) copolymer *10 | — | 0.5 | 30 | — | 0.5 | 30 |
| Total | 100 | 100 | 100 | 100 | 100 | 100 |
| L value | 13.04 | 11.68 | 21 | 66.31 | 63.32 | 50.89 |
| a value | 0.08 | 0.3 | 10.66 | −1.09 | 1.6 | 54.37 |
| b value | −2.11 | −1.35 | 5.84 | −3.16 | −2.85 | −1.33 |
| Chroma: $(a2 + b2)1/2$ | 2.1 | 1.4 | 12.2 | 3.3 | 3.3 | 54.4 |
| Color development | A | A | B | A | A | B |

The compositions 1 to 3 contained dextrin palmitate as described in Table 7. Dextrin palmitate is a gelling agent. The compositions 1 to 3 were in a semi-solid form (gel form).

The compositions 4 to 6 contained an (ethylene/propylene) copolymer as described in Table 7. The (ethylene/propylene) copolymer is a hydrocarbon solid oil. The compositions 4 to 6 were in a solid form.

As shown in Table 7 and FIG. 2, the compositions 1 and 2 were colorless. In other words, in the compositions 1 and 2, the red color development due to Red No. 218 was suppressed. In contrast, the composition 3 exhibited red. In other words, in the composition 3, the red color development due to Red No. 218 was not suppressed. These results reveal that when a large amount of the (vinylpyrrolidone/hexadecene) copolymer as an oil agent is contained, the red color due to Red No. 218 is developed, whereas when diisostearyl malate accounts for a large fraction of the oil agent, the red color development due to Red No. 218 is suppressed.

As shown in Table 7 and FIG. 2, the compositions 4 and 5 were colorless. In other words, in the compositions 4 and 5, the red color development due to Red No. 218 was suppressed.

The compositions 4 and 5 were in a solid form (wax form). Hence, in the case of cosmetics in a solid dosage form, it was also ascertained that when diisostearyl malate accounts for a large fraction of the oil agent, the red color development due to Red No. 218 is suppressed as with the gel form.

In contrast, the composition 6 exhibited red. In other words, in the composition 6, the red color development due to Red No. 218 was not suppressed.

The composition 6 was in a solid form (wax form). Hence, even when the dosage form of cosmetics is solid, it was ascertained that when a large amount of the (vinylpyrrolidone/hexadecene) copolymer as an oil agent is contained, the red color development due to Red No. 218 is not suppressed as with the gel form.

As described above, it was ascertained that suppression of red color development by a combination of a red dye and a particular oil agent is achieved not only by the compositions in a gel dosage form adopted in <1. Evaluation of color development by composition comprising dye and oil agent> but also by the compositions in a solid form.

7. Cheek Rouge Containing Red No. 218 and Red No. 223

A cheek rouge having the following formulation was produced in accordance with the following production method.

| (Component) | (%) |
|---|---|
| (1) Dextrin palmitate *20 | 3 |
| (2) Mineral oil *11 | 20 |
| (3) Methylphenylpolysiloxane *14 | 5 |
| (4) Tritridecyl trimellitate *5 | 10 |
| (5) Polyglyceryl-2 triisostearate (emery type) *3 | 1 |
| (6) Silicone-coated mica | remainder |
| (7) Hollow silica *22 | 10 |
| (8) Silica-coated titanium oxide | 2 |
| (9) R218 *1 | 0.03 |
| (10) R223 *17 | 0.01 |
| (11) Silica dimethyl silylate *2 | 0.4 |
| (12) (Acrylic acid/alkyl (C10-30) acrylate) copolymer *18 | 0.08 |
| (13) Proteoglycan | 0.01 |
| (14) Corn oil | 0.02 |
| (15) Rose hip oil | 0.02 |

*22 Silica micro bead BA-1 (manufactured by JGC Catalysts and Chemicals Ltd.)

(Production Method)
A. Components (1) to (5) are homogeneously dissolved at 80° C.
B. To A, components (6) to (15) are added and homogeneously mixed.
C. B is heated to 100° C. and is packed in a container, giving a cheek rouge.

The resulting cheek rouge was colorless in appearance but developed a color on application.

8. Eye Shadow Containing Red No. 218 and Red No. 223

An eye shadow having the following formulation was produced in accordance with the following production method.

| (Component) | (%) |
|---|---|
| (1) Trimethylsiloxysilicate *23 | 5 |
| (2) Tritridecyl trimellitate *5 | 10 |
| (3) Methylphenylpolysiloxane *14 | 5 |
| (4) Isododecane | 20 |
| (5) Silicone-coated talc | 10 |
| (6) Silicone-coated mica | remainder |
| (7) Silicone-coated titanium oxide | 2 |
| (8) R218 *1 | 0.03 |
| (9) R223 *17 | 0.01 |
| (10) Silica dimethyl silylate *2 | 0.4 |
| (11) (Acrylic acid/alkyl (C10-30) acrylate) copolymer *18 | 0.08 |
| (12) Apricot kernel oil | 0.02 |
| (13) Olive oil | 0.02 |

*23 SR1000 (manufactured by Momentive Performance Materials Inc.)

(Production Method)
A. Components (1) to (4) are homogeneously dissolved.
B. To A, components (5) to (13) are added and homogeneously mixed.
C. B is packed in a container, giving an eye shadow.

The resulting eye shadow was colorless in appearance but developed a color on application.

The invention claimed is:

1. A colorless oily makeup cosmetic containing:
   (a) one or two dyes selected from Red No. 218 and Red No. 223; wherein content rate of the component (a) is 0.01 to 1.0% by mass relative to the mass of the cosmetic and
   (b) an oil agent, wherein the mixture of the (a) and the (b) are at a mass ratio (a):(b) of 0.1:100, the mixture having a difference of 0.2 or less between a maximum absorbance and a minimum absorbance in a wavelength region of 500 to 600 nm, and wherein component (b) is polyglyceryl-2 triisostearate having methyl-branched isostearic acid groups wherein content rate of the component (b) is 65 to 99.9% by mass relative to a mass of the cosmetic and wherein said colorless cosmetic develops a red color on application onto skin and/or a lip.

2. The cosmetic according to claim 1, wherein the cosmetic further contains an oily gelling agent.

3. The cosmetic according to claim 1, wherein the cosmetic is liquid at 25° C.

4. The cosmetic according to claim 1, wherein the cosmetic has a dynamic viscosity of 10,000 to 20,000 cs at 25° C.

* * * * *